(12) United States Patent
Tang et al.

(10) Patent No.: US 7,539,281 B2
(45) Date of Patent: May 26, 2009

(54) METHODS AND APPARATUS FOR RECONSTRUCTION IN HELICAL CONE BEAM VOLUMETRIC CT

(75) Inventors: Xiangyang Tang, Waukesha, WI (US); Jiang Hsieh, Brookfield, WI (US); Roy Arnulf Helge Nilsen, Mcnomonee Falls, WI (US)

(73) Assignee: General Electric Company, Schenectady, NY (US)

( * ) Notice: Subject to any disclaimer, the term of this patent is extended or adjusted under 35 U.S.C. 154(b) by 363 days.

(21) Appl. No.: 10/966,881

(22) Filed: Oct. 15, 2004

(65) Prior Publication Data

US 2006/0083344 A1    Apr. 20, 2006

(51) Int. Cl.
*A61B 6/03* (2006.01)
(52) U.S. Cl. ............................... 378/15; 378/4; 378/901
(58) Field of Classification Search ...... 378/4, 378/15, 210, 901; 382/128–131
See application file for complete search history.

(56) References Cited

U.S. PATENT DOCUMENTS

| | | | |
|---|---|---|---|
| 6,014,419 A | 1/2000 | Hu | |
| 6,018,561 A | 1/2000 | Tam | |
| 6,078,638 A | 6/2000 | Sauer et al. | |
| 6,084,937 A | 7/2000 | Tam et al. | |
| 6,097,784 A | 8/2000 | Tuy | |
| 6,108,575 A * | 8/2000 | Besson | 600/425 |
| 6,275,561 B1 * | 8/2001 | Danielsson | 378/15 |
| 6,324,245 B1 | 11/2001 | Tam | |
| 6,529,575 B1 * | 3/2003 | Hsieh | 378/4 |
| 6,574,297 B2 | 6/2003 | Tam | |
| 6,574,299 B1 * | 6/2003 | Katsevich | 378/15 |
| 6,678,346 B2 | 1/2004 | Hsieh | |
| 6,775,347 B2 | 8/2004 | Hsieh et al. | |
| 7,180,975 B2 * | 2/2007 | Heuscher et al. | 378/4 |
| 2004/0028173 A1 * | 2/2004 | van de Haar | 378/4 |
| 2004/0252806 A1 * | 12/2004 | Taguchi et al. | 378/4 |
| 2004/0264630 A1 * | 12/2004 | Bruder et al. | 378/15 |
| 2006/0233294 A1 * | 10/2006 | Bontus et al. | 378/4 |

OTHER PUBLICATIONS

Katsevich et al., Evaluation and empirical analysis of an exact FBP algorithm for spiral cone-beam CT, SPIE, vol. 5032, Proceeding of Medical Imaging 2003: Image Processing, Feb. 2003, p. 663-674.*
Tam et al., Exact cone beam CT with a spiral scan, 1998, Phys. Med. Biol., 43, pp. 1015-1024.*
Kudo et al., New Approximate Filtered Backprojection Algorithm for Helical Cone-Beam CT with Redundant Data, Oct. 19-25, 2003, IEEE 2003 Nuclear Science Symposium Conference Record, vol. 5, pp. 3211-3215.*
Kudo et al., Exact and approximate algorithms for helical cone-beam CT, Jun. 17, 2004, Physics in Medicine and Biology, vol. 49, pp. 2913-2931.*

* cited by examiner

*Primary Examiner*—Edward J Glick
*Assistant Examiner*—John M Corbett
(74) *Attorney, Agent, or Firm*—Armstrong Teasdale LLP

(57) ABSTRACT

A method for reconstructing an image of an object utilizing a cone-beam volumetric computed tomographic imaging apparatus includes helically scanning the object with a radiation source utilizing the cone-beam volumetric computed tomographic imaging apparatus, selecting radiation beams emitted by the radiation source passing through a pixel P, a Tam-window, and a Katsevich window, filtering the selected projection data, and reconstructing an image of the object utilizing the filtered selected projection data including projection data within the Katsevich window and outside the Tam-window.

20 Claims, 6 Drawing Sheets

METHODS AND APPARATUS FOR RECONSTRUCTION IN HELICAL CONE BEAM VOLUMETRIC CT

BACKGROUND OF THE INVENTION

This invention relates generally to methods and apparatus for reconstruction of volumetric computed tomographic (CT) images, and more particularly to methods and apparatus for extending exact helical cone beam reconstruction algorithm for volumetric CT to improve noise characteristics and dose efficiency.

In at least one known multi-detector row CT imaging systems, two-dimensional (2D) algorithms have been used to reconstruct tomographic images based on an approximation of cone beam (CB) geometry into fan beam (FB) geometry. As CB volumetric CT (VCT) technology becomes more prevalent, maintaining reconstruction accuracy has become more challenging. As a result of a significantly larger cone angle, CB-to-FB geometry approximations result in significant artifacts. To combat these artifacts, three dimensional (3D) reconstruction algorithms can be used in CB VCT. One such algorithm has been proposed by A. Katsevich in "Analysis of an exact inversion algorithm for spiral cone-beam CT," Physics in Medicine & Biology vol. 47, pp. 2583-2598, 2002. The Katsevich algorithm has drawn extensive attention, because its shift-invariant filtered back projection structure is compatible with that employed by currently commercial CT scanners.

However, like some other exact CB reconstruction algorithms, the Katsevich algorithm may not make use of projection data very efficiently. To maintain reconstruction accuracy, it uses the Tam-window to handle data redundancy by discarding all redundant projection data. In fact, the projection data needed by the Katsevich algorithm for filtering occupy a detector area larger than the Tam-window, but only the filtered data within the Tam-window contribute to CB reconstruction. This means that, the projection data filtered by the Katsevich algorithm but outside the Tam-window are wasted, resulting in degraded noise characteristics and x-ray dose efficiency. The amount of wasted projection data is helical pitch-dependent. The larger the helical pitch is, the more the projection data are wasted.

BRIEF DESCRIPTION OF THE INVENTION

In one aspect, a method for reconstructing an image of an object utilizing a cone-beam volumetric computed tomographic imaging apparatus. The method includes helically scanning the object with a radiation source utilizing the cone-beam volumetric computed tomographic imaging apparatus, selecting radiation beams emitted by the radiation source passing through a pixel P, a Tam-window, and a Katsevich window, filtering the selected projection data, and reconstructing an image of the object utilizing the filtered selected projection data including projection data within the Katsevich window and outside the Tam-window.

In another aspect, there is provided a cone-beam volumetric computed tomographic imaging apparatus. The apparatus is configured to helically scan an object to be imaged with a radiation source utilizing the cone-beam volumetric computed tomographic imaging apparatus, select radiation beams emitted by the radiation source passing through a pixel P, a Tam-window, and a Katsevich window, filter the selected projection data, and reconstruct an image of the object utilizing the filtered selected projection data including projection data within the Katsevich window and outside the Tam-window.

In yet another aspect, there is provided a computer-usable medium having a computer-readable program embodied thereon. The program is configured to instruct a computer to interpolate projection data of a scan of an object wherein the object is helically scanned with a radiation source utilizing a cone-beam volumetric computed tomographic imaging apparatus, the interpolation is configured to select radiation beams emitted by the radiation source passing through a pixel P, a Tam-window, and a Katsevich window, to filter the selected projection data and reconstruct an image of the object utilizing the filtered selected projection data including projection data within the Katsevich window and outside the Tam-window

DETAILED DESCRIPTION OF THE INVENTION

Figure 1:
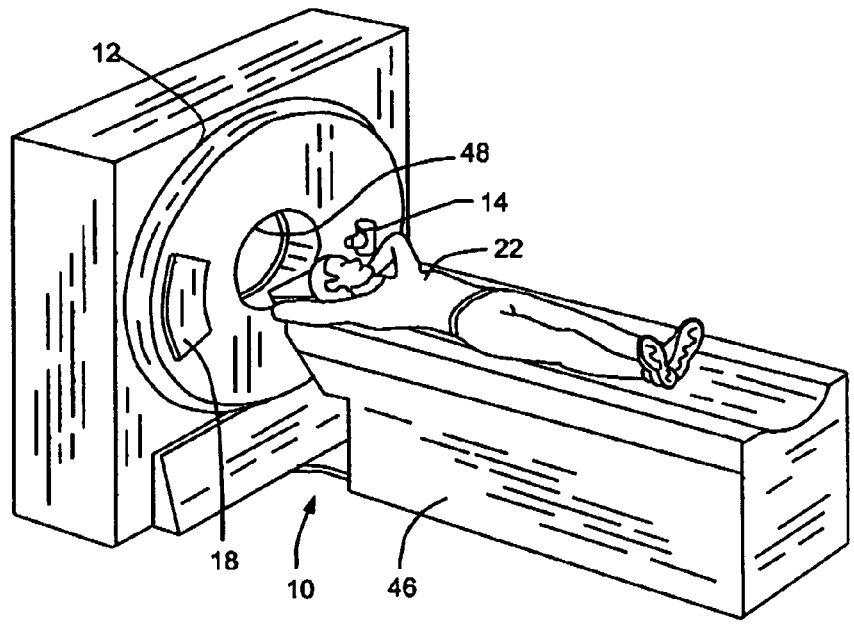
FIG. 1 is a pictorial drawing representative of some configurations of CT imaging apparatus of the present invention.

In some known CT imaging system configurations, an x-ray source projects a fan-shaped beam which is collimated to lie within an X-Y plane of a Cartesian coordinate system and generally referred to as an "imaging plane". The x-ray beam passes through an object being imaged, such as a patient. The beam, after being attenuated by the object, impinges upon an array of radiation detectors. The intensity of the attenuated radiation beam received at the detector array is dependent upon the attenuation of an x-ray beam by the object. Each detector element of the array produces a separate electrical signal that is a measurement of the beam intensity at the detector location. The intensity measurements from all the detectors are acquired separately to produce a transmission profile.

In third generation CT systems, the x-ray source and the detector array are rotated with a gantry within the imaging plane and around the object to be imaged such that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles, or view angles, during one revolution of the x-ray source and detector.

In an axial scan, the projection data is processed to construct an image that corresponds to a two-dimensional slice taken through the object. One method for reconstructing an image from a set of projection data is referred to in the art as the filtered backprojection technique. This process converts the attenuation measurements from a scan into integers called "CT numbers" or "Hounsfield units" (HU), which are used to control the brightness of a corresponding pixel on a cathode ray tube display.

To reduce the total scan time, a "helical" scan may be performed. To perform a "helical" scan, the patient is moved while the data for the prescribed number of slices is acquired. Such a system generates a single helix from a fan beam helical scan. The helix mapped out by the fan beam yields projection data from which images in each prescribed slice may be reconstructed.

Reconstruction algorithms for helical scanning typically use helical weighing algorithms that weight the collected data as a function of view angle and detector channel index. Specifically, prior to a filtered backprojection process, the data is weighted according to a helical weighing factor, which is a function of both the gantry angle and detector angle. The weighted data is then processed to generate CT numbers and to construct an image that corresponds to a two-dimensional slice taken through the object.

To further reduce the total acquisition time, multi-slice CT has been introduced. In multi-slice CT, multiple rows of projection data are acquired simultaneously at any time instant. When combined with helical scan mode, the system generates a single helix of cone beam projection data. Similar to the single slice helical, weighting scheme, a method can be derived to multiply the weight with the projection data prior to the filtered backprojection algorithm.

As used herein, an element or step recited in the singular and proceeded with the word "a" or "an" should be understood as not excluding plural said elements or steps, unless such exclusion is explicitly recited. Furthermore, references to "one embodiment" of the present invention are not intended to be interpreted as excluding the existence of additional embodiments that also incorporate the recited features.

Also as used herein, the phrase "reconstructing an image" is not intended to exclude embodiments of the present invention in which data representing an image is generated but a viewable image is not. However, many embodiments generate (or are configured to generate) at least one viewable image.

Figure 2:
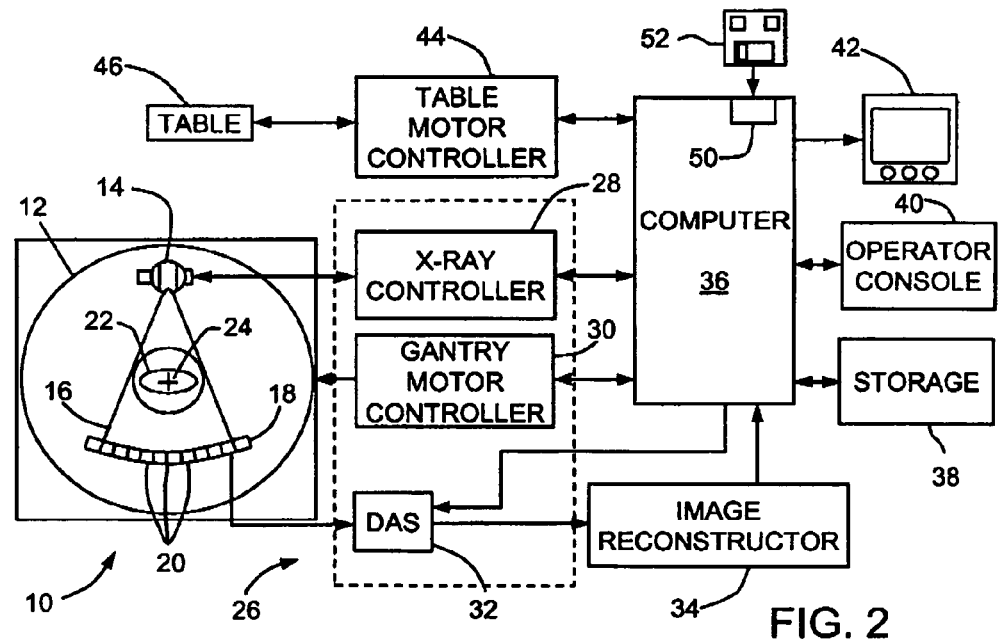
FIG. 2 is a functional block diagram representative of the CT imaging apparatus of FIG. 1.

Referring to FIGS. 1 and 2, a multi-slice scanning imaging system, for example, a Computed Tomography (CT) imaging system 10, is shown as including a gantry 12 representative of a "third generation" CT imaging system. Gantry 12 has an x-ray tube 14 (also called x-ray source 14 herein) that projects a beam of x-rays 16 toward a detector array 18 on the opposite side of gantry 12. Detector array 18 is formed by a plurality of detector rows (not shown) including a plurality of detector elements 20 which together sense the projected x-rays that pass through an object, such as a medical patient 22 between array 18 and source 14. Each detector element 20 produces an electrical signal that represents the intensity of an impinging x-ray beam and hence can be used to estimate the attenuation of the beam as it passes through object or patient 22. During a scan to acquire x-ray projection data, gantry 12 and the components mounted therein rotate about a center of rotation 24. FIG. 2 shows only a single row of detector elements 20 (i.e., a detector row). However, multi-slice detector array 18 includes a plurality of parallel detector rows of detector elements 20 such that projection data corresponding to a plurality of quasi-parallel or parallel slices can be acquired simultaneously during a scan.

Rotation of components on gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of components on gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high-speed image reconstruction. The reconstructed image is applied as an input to a computer 36, which stores the image in a storage device 38. Image reconstructor 34 can be specialized hardware or computer programs executing on computer 36.

Computer 36 also receives commands and scanning parameters from an operator via console 40 that has a keyboard. An associated cathode ray tube display 42 or other suitable display type allows the operator to observe the reconstructed image and other data from computer 36. The operator supplied commands and parameters are used by computer 36 to provide control signals and information to DAS 32, x-ray controller 28, and gantry motor controller 30. In addition, computer 36 operates a table motor controller 44, which controls a motorized table 46 to position patient 22 in gantry 12. Particularly, table 46 moves portions of patient 22 through gantry opening 48.

In one embodiment, computer 36 includes a storage device 50, for example, but not limited to, a floppy disk drive, CD-ROM drive, DVD drive, magnetic optical disk (MOD) device. In another embodiment, computer 36 executes instructions stored in firmware (not shown). Computer 36 is programmed to perform functions described herein, and as used herein, the term computer is not limited to just those integrated circuits referred to in the art as computers, but broadly refers to computers, processors, microcontrollers, microcomputers, programmable logic controllers, application specific integrated circuits, and other programmable circuits, and these terms are used interchangeably herein. Although the specific embodiment mentioned above refers to a third generation CT system, the methods described herein equally apply to fourth generation CT systems (stationary detector—rotating x-ray source) and fifth generation CT systems (stationary detector and x-ray source). Additionally, it is contemplated that the benefits of the invention accrue to imaging modalities other than CT. Additionally, although the herein described methods and apparatus are described in a medical setting, it is contemplated that the benefits of the invention accrue to non-medical imaging systems such as those systems typically employed in an industrial setting or a transportation setting, such as, for example, but not limited to, a baggage scanning system for an airport or other transportation center.

Some configurations of the herein described extend the original Katsevich algorithm. An exact helical CB reconstruction algorithm, called the extended Katsevich algorithm, is disclosed here. The extended Katsevich algorithm makes use of all the projection data required by the original Katsevich algorithm, rather than just that within the Tam-window, resulting in significantly improved noise characteristics and noise efficiency.

Figure 3:
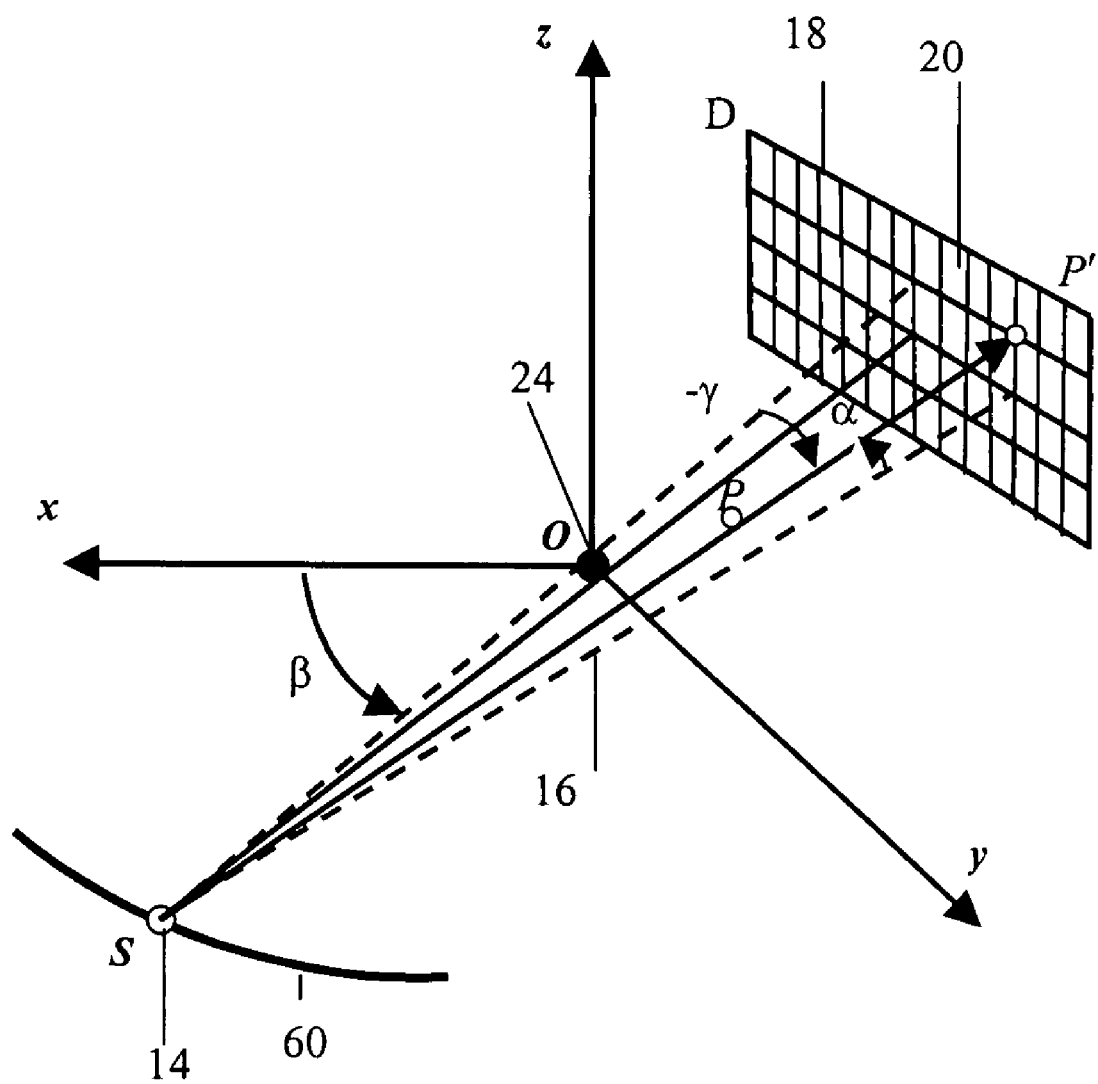
FIG. 3 is a representation of the geometry of a CB VCT apparatus.

There exist two versions of the original Katsevich CB reconstruction algorithms. Each is based on the geometry of a CB VCT using a flat panel detector array 18 as represented in FIG. 3. A radiation beam 16 emanates from a focal spot S of radiation source 14. In many computed tomographic imaging systems 10, radiation detector array 18 is an x-ray detector array, radiation beam 16 is an x-ray beam, and radiation source 14 is an x-ray source, and will be referred to as such herein. However, configurations of the herein described are not limited to the use of x-ray radiation. X-ray beam 16 passes through a point P, and has a view angle β, a fan angle γ, and a cone angle α. Point P' represents the projection of point P in flat panel detector array D (or 18).

The first version is analytically expressed as $$f(x) = -\frac{1}{2\pi^2} \int_{I_{Pl}(x)} \frac{1}{|x - y(x)|} w_T(y(q), x) \int_0^{2\pi} \frac{\partial}{\partial q} D_f(y(q), \Theta(s, x, \gamma)) \bigg|_{q=s} \frac{d\gamma}{\sin\gamma} ds, \quad (1)$$

where y(s) represents the source focal spot, x the pixel to be reconstructed and γ the fan angle within the Katsevich plane.

where u and v are the horizontal and vertical axes, respectively, in the flat panel x-ray detector 18, and L is the distance from source focal spot S of x-ray source 14 to detector D (or 18), R is the distance from source focal spot S to the axis z of helical source trajectory 60, and h is the distance proceeded per helical turn.

Figure 4:
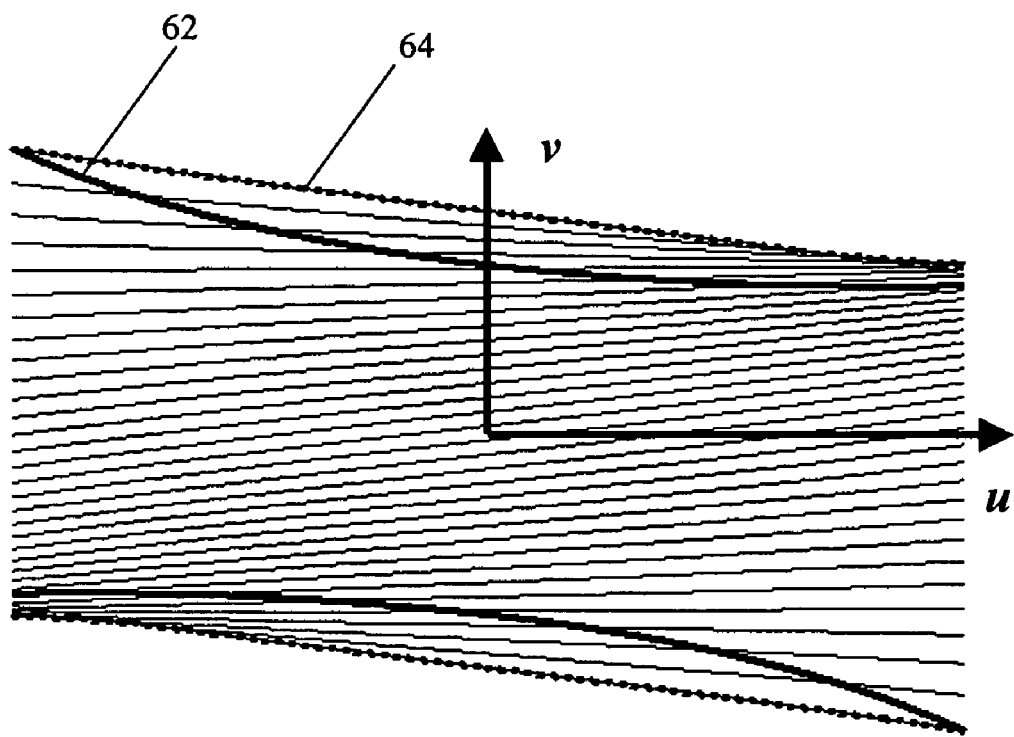
FIG. 4 is an example of a Tam-window and a Katsevich window.

FIG. 4 is an example of a Tam-window 62 and a Katsevich window 64. The upper and lower boundaries of Tam-window 62 are determined by the intersection of the x-ray beams emanating from the source and passing through the upper and lower helical turns. However, all the projection data involved in the filtering operation of the original Katsevich algorithm occupy the area defined by the dotted curves 64 (namely Katsevich window hereafter). Katsevich window 64 is significantly larger than Tam-window 62. This means that, the projection data distributing between Tam-window 62 and Katsevich window 64 is demanded by the original Katsevich algorithm, but make no contribution to reconstruction, i.e., are wasted in terms of noise characteristics or dose efficiency.

Figure 5:
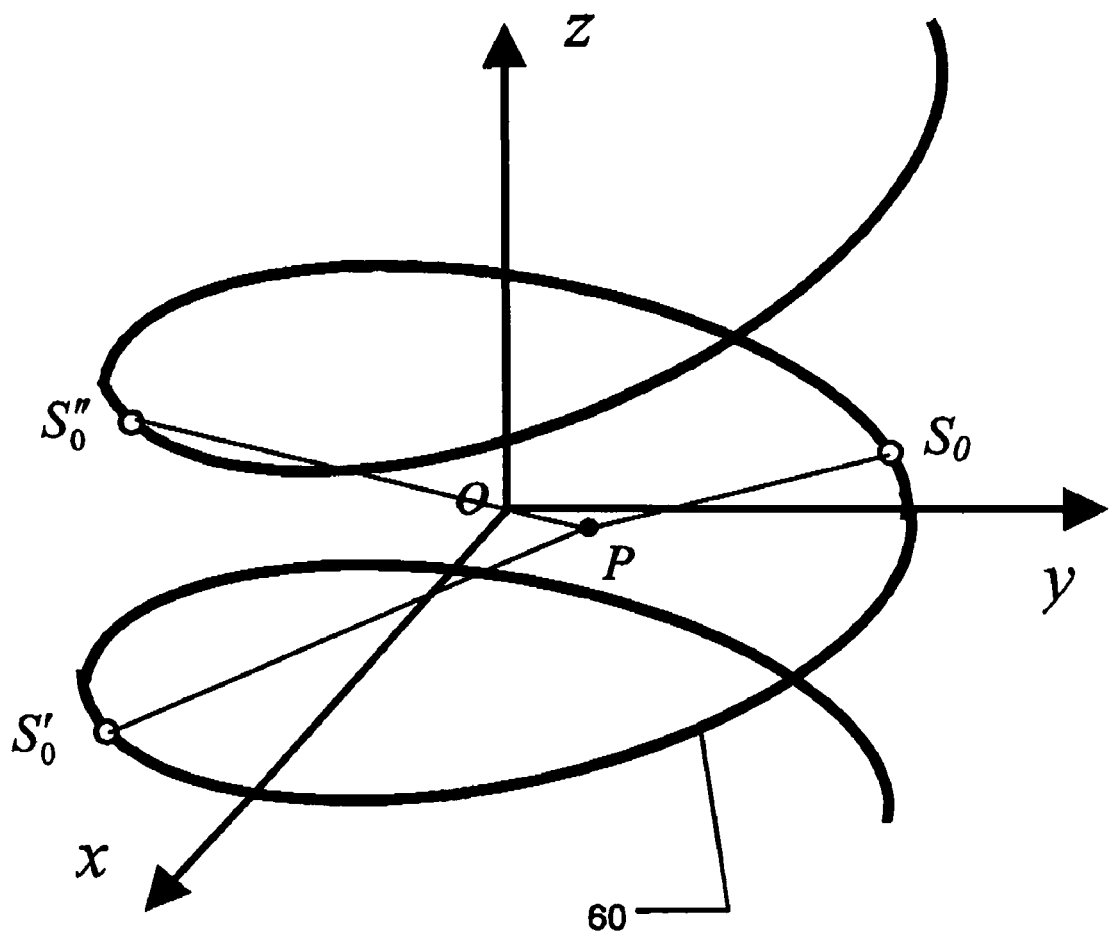
FIG. 5 is a schematic diagram showing the geometry of direct-ray and its two conjugate-rays within one turn of a helix, where ray $S_0P$ is the direct ray determined by $(\alpha_0, \beta_0, \gamma_0)$, ray $S'_0P$ is one of the conjugate ray determined by $(\alpha'_0, \beta'_0-\pi, \gamma'_0)$, and $S''_0P$ is the other conjugate ray determined by $(\alpha''_0, \beta''_0+\pi, \gamma''_0)$.

The extended Katsevich algorithm herein described allows the projection data between Tam-window 62 and Katsevich window 64 contribute to a CB reconstruction. As shown in FIG. 3, a ray 16 emanating from a source focal spot S and passing through the pixel to be reconstructed is called a direct ray SP and determined by its view angle β, fan angle γ, and cone angle α. A conjugate ray $SP^c$ associated with the direct ray SP possesses a view angle β=β±iπ (i=1, 2, 3, ... ). Generally, as shown in FIG. 5, there exist infinite conjugate $$f(x) = -\frac{1}{2\pi^2} \left\{ \left[ \frac{1}{|x - y(s)|} \int_0^{2\pi} D_f(y(s), \Theta(s, x, y)) \frac{d\gamma}{\sin\gamma} \right]_{s=s_b(x)}^{s=s_t(x)}, \right. \quad (2)$$

$$- \int_{I_{Pl}(x)} \left( \frac{\partial}{\partial s} \frac{1}{|x - y(s)|} \right) w_T(y(s), x) \int_0^{2\pi} D_f(y(s), \Theta(s, x, \gamma)) \frac{d\gamma}{\sin\gamma} ds$$

$$- \int_{I_{Pl}(x)} \frac{\beta_s'(s, x) \cdot u(s, x)}{|x - y(s)|} w_T(y(s), x) \int_0^{2\pi} (\nabla_{u(s,x)} D_f)(y(s), \Theta(s, x, \gamma)) \cot\gamma\, d\gamma ds$$

$$- \int_{I_{Pl}(x)} \frac{e_s'(s, x) \cdot u(s, x)}{|x - y(s)|} w_T(y(s), x) \int_0^{2\pi} (\nabla_{u(s,x)} D_f)(y(s), \Theta(s, x, \gamma)) d\gamma ds$$

$$\left. - \int_{I_{Pl}(x)} \frac{\beta_s'(s, x) \cdot e(s, x)}{|x - y(s)|} w_T(y(s), x) \int_0^{2\pi} \left( \frac{\partial}{\partial \gamma} D_f(y(s), \Theta(s, x, \gamma)) \right) \frac{d\gamma}{\sin\gamma} \right\} ds$$

where $$e(s, x) = \beta(s, x) \times u(s, x) \quad (3)$$

$$\Theta(s, x, \gamma) = \cos\gamma \beta(s, x) + \sin\gamma e(s, x) \quad (4)$$

$$(\nabla_u D_f)(y(s), \Theta) = \frac{\partial}{\partial t} D_f\left(y(s), \sqrt{1-t^2}\, \Theta + tu\right)\bigg|_{t=0}, \Theta \in u^\perp \quad (5)$$

In both versons, the Tam-window $w_T(y(s),x)$, which is analytically expressed below, is utilized to handle data redundancy, $$v = \frac{Lh}{R}\left(1 + \frac{u^2}{L^2}\right)\left[\frac{\pi}{2} \pm \arctan\left(\frac{u}{L}\right)\right] \quad (6)$$

rays $SP^c$ associated with a direct ray SP. Without losing generality, one can always constrain ourselves within one turn of a helix, and such that only a direct ray SP with view angle β and one of its adjacent conjugate rays $SP^c$ with view angle $β_c$ ($β_c$=β+π or or $β_c$=β−π) are taken into account. Consequently, the extended Katsevich algorithm can be analytically expressed as $$f(x) = -\frac{1}{2\pi^2} \int_0^{2\pi} w_{WW}(y(q), x) \int_0^{2\pi} \frac{\partial}{\partial q} D_f(y(q), \Theta(s, x, \gamma))\Big|_{q=s} \frac{d\gamma}{\sin\gamma} ds \qquad (7)$$

$$f(x) = -\frac{1}{2\pi^2} \Bigg\{ \left[ \frac{1}{|x-y(s)|} \int_0^{2\pi} D_f\left(y(s), \Theta(s, x, \gamma)\right) \frac{d\gamma}{\sin\gamma} ds \right]_{s=s_b(x)}^{s=s_t(x)}, \qquad (8)$$

$$- \int_0^{2\pi} \left( \frac{\partial}{\partial s} \frac{1}{|x-y(s)|} \right) w_{WW}(y(s), x) \int_0^{2\pi} D_f(y(s), \Theta(s, x, \gamma)) \frac{d\gamma}{\sin\gamma} ds$$

$$- \int_0^{2\pi} \frac{\beta'_s(s, x) \cdot u(s, x)}{|x-y(s)|} w_{WW}(y(s), x) \int_0^{2\pi} (\nabla_{u(s,x)} D_f)(y(s), \Theta(s, x, \gamma)) \cot\gamma \, d\gamma ds$$

$$- \int_0^{2\pi} \frac{e'_s(s, x) \cdot u(s, x)}{|x-y(s)|} w_{WW}(y(s), x) \int_0^{2\pi} (\nabla_{u(s,x)} D_f)(y(s), \Theta(s, x, \gamma)) d\gamma ds$$

$$- \int_0^{2\pi} \frac{\beta'_s(s, x) \cdot e(s, x)}{|x-y(s)|} w_{WW}(y(s), x) \int_0^{2\pi} \left( \frac{\partial}{\partial \gamma} D_f(y(s), \Theta(s, x, \gamma)) \right) \frac{d\gamma}{\sin\gamma} \Bigg\} ds$$

respectively, where $w_{WW}(y(s),x)$ is a view weighting and windowing function that can be analytically expressed as $$w_{WW}(y(s), x) = \begin{cases} 0 & \text{Condition I} \\ 1 & \text{Condition II} \\ \frac{1}{2} & \text{Condition III} \end{cases} \qquad (9)$$

Condition I corresponds to the situation that both the direct ray and its conjugate ray are outside Katsevich window 64, Condition II corresponds to the situation that either the direct ray or its conjugate ray is within Katsevich window 64, and Condition III corresponds to the situation that both the direct and conjugate rays are inside Katsevich window 64.

In fact, the view weighting and windowing function given in eq. (9) is a special case for the extended Katsevich algorithm, which is the best from the perspective of noise characteristics and dose efficiency. A general view weighting and function for the extended Katsevich algorithm can be expressed as $$w_{WW}(y(s), x) = \begin{cases} 0 & \text{Condition I} \\ 1 & \text{Condition II} \\ \frac{\tan^k \alpha_c}{\tan^k \alpha + \tan^k \alpha_c} & \text{Condition III} \end{cases} \qquad (10)$$

where k is real number larger than 0, and can be adjusted for practical optimization.

Furthermore, the view weighting and windowing function given in eq. (10) is still a special case for the extended Katsevich algorithm. A more general view weighting and windowing function for the extended Katsevich algorithm can be expressed as $$w_{WW}(y(s), x) = \begin{cases} 0 & \text{Condition I} \\ 1 & \text{Condition II} \\ \frac{g_k(\alpha_c)}{g_k(\alpha) + g_k(\alpha_c)} & \text{Condition III} \end{cases} \qquad (11)$$

where k is real number larger than 0.

$g_k(\alpha)$ is a positive valued monotonically increasing function of $\alpha$, i.e., $$g_k(\alpha) > 0$$

$$g_k(\alpha_1) < g_k(\alpha_2) \text{ while } 0 < \alpha_1 < \alpha_2.$$

$g_k(\alpha_c)$ is also a positive valued monotonically increasing function of $\alpha_c$, i.e., $$g_k(\alpha_c) > 0$$

$$g_k(\alpha_{c1}) < g_k(\alpha_{c2}) \text{ while } 0 < \alpha_{c1} < \alpha_{c2}.$$

There exist two major differences between the extended Katsevich algorithm shown in (7)~(9) and the original Katsevich algorithm in (1)~(2): (a) the original Katsevich algorithm uses a pixel-wise integral interval called the PI interval, but the extended Katsevich algorithm uses the same $2\pi$ interval for all pixel to be reconstructed; (b) the original Katsevich algorithm uses a window function (Tam-window 62) only, but the extended Katsevich algorithm uses a view weighting and windowing function as specified in (10). These two differences together that make the extended Katsevich algorithm outperform the original Katsevich algorithm from the perspective of noise characteristics and dose efficiency.

Figure 6:
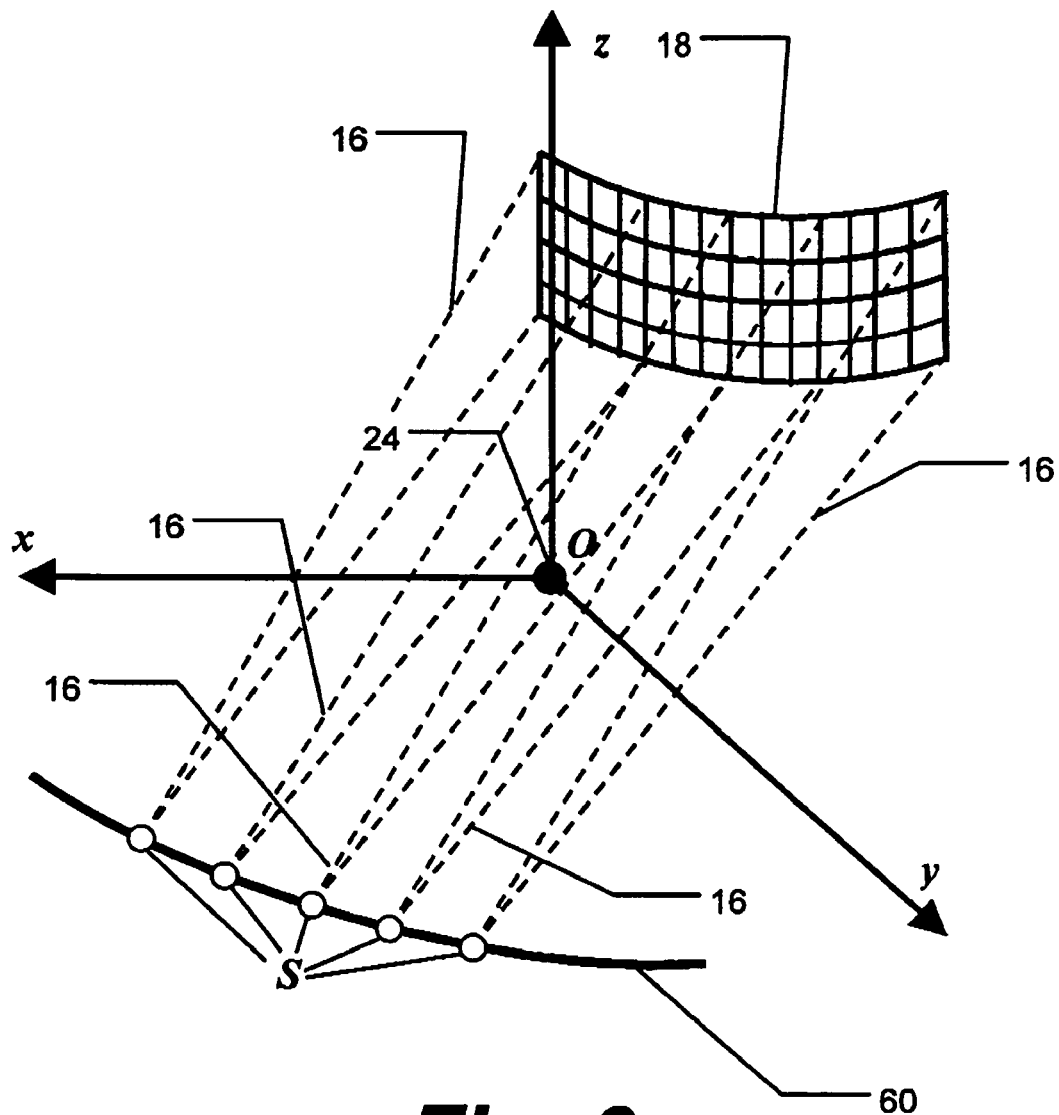
FIG. 6 is a schematic diagram showing the geometry of cone-parallel beam, which can be obtained from the CB projection data acquired by the geometry shown in FIG. 3 through row-wise fan-to-parallel rebinning.

Finally, it has to be pointed out that, although it is expressed in the geometry in which a flat panel x-ray detector 18 is utilized, the extended Katsevich algorithm can also be expressed in the geometry where a cylindrical x-ray detector 18 is utilized by carrying out coordinate system transformation. Moreover, although it is expressed in the natural CB geometry, the extended Katsevich algorithm can also be expressed in the so-called cone-parallel beam geometry (see FIG. 6). A focal point S is illustrated at a few positions along a trajectory 60, representing points that focal point S occupies at different times. Several x-ray beams 16 are also illustrated, showing the geometry of the x-ray beam emitted by x-ray source 14 at each different location represented in FIG. 6. The cone-parallel beam geometry is implemented using row-wise fan-to-parallel rebinning.

Figure 7:
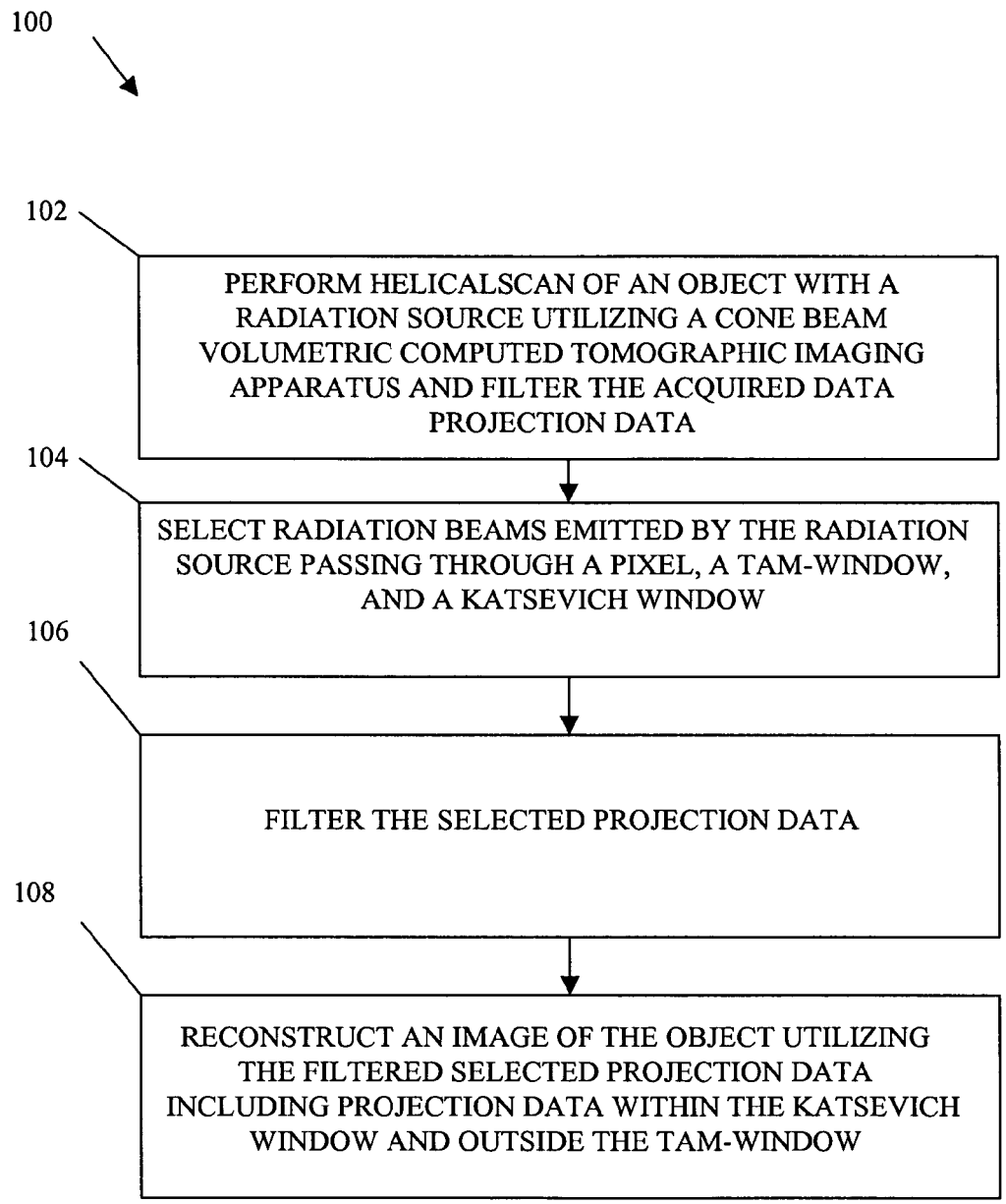
FIG. 7 is a flow chart representative of a method for reconstructing an image of an object in configurations of the present invention.

Thus, and referring to flow chart 100 of FIG. 7, a technical result of the herein described is achieved in some configurations by a user initiating a helical scan of an object 22 (for example, a medical patient) with a radiation source such as radiation source 14 utilizing a cone beam volumetric computed tomographic imaging apparatus 10 at 102 and filtering the acquired projection data. Radiation beams 16 emitted by radiation source 14 are then selected at 104 passing through a pixel P, a Tam-window 62, and a Katsevich window 64. (By "selecting radiation beams," it is meant that a determination is made as to the projection data that is to be used for reconstructing the image of the object, for example, by applying an extended Katsevich algorithm to projection data.) In some configurations, selecting radiation beams passing through pixel P by applying a view weighting and windowing function to projection data to include conjugate projection data contributing to reconstruction. At 106, the selected projection is filtered. At 108, an image of the object is reconstructed utilizing the filtered selected projection data including projection data within the Katsevich window and outside the Tam-window. In some configurations in which a view weighting and windowing function takes values of 0, 1, and ½, the reconstruction is performed with the use of redundant projection data from selected radiation beams between the Tam-window and the Katsevich window. In some configurations, reconstructing an image of the object comprises utilizing the extended Katsevich algorithm filtered projection data from in which redundancy has been maintained through the use of the view weighting and windowing function.

In some configurations, view weighting and windowing and image reconstruction are performed, for example, by one or more of image reconstructor 34, and/or computer 36, utilizing storage device 38. The resulting images can be displayed on display 42.

It will thus be appreciated that configurations of the present invention provide alternatives to the original Katsevich algorithm for CB volumetric CT utilizing exact helical CB reconstruction. Moreover, by utilizing redundant projection data, noise characteristics or dose efficiency are substantially improved.

While the invention has been described in terms of various specific embodiments, those skilled in the art will recognize that the invention can be practiced with modification within the spirit and scope of the claims.

What is claimed is:

1. A mathematically exact method for reconstructing an image of an object utilizing a cone-beam volumetric computed tomographic imaging apparatus, said method comprising:

helically scanning the object with a radiation source utilizing the cone-beam volumetric computed tomographic imaging apparatus;

selecting radiation beams emitted by the radiation source passing through a pixel P, a Tam-window, and a Katsevich window;

filtering the selected projection data using a 2π interval for each pixel that is to be reconstructed;

reconstructing an image of the object utilizing the filtered selected projection data including projection data within the Katsevich window and outside the Tam-window;

outputting the reconstructed image.

2. A method in accordance with claim 1 wherein said reconstructing an image of the object is performed utilizing redundant projection data from the selected radiation beams between the Tam-window and the Katsevich window.

3. A method in accordance with claim 1 wherein said selecting radiation beams emitted by the radiation source includes selecting direct rays and at least one conjugate ray wherein the radiation source is an x-ray radiation source.

4. A method in accordance with claim 1 wherein said selecting radiation beams passing through a pixel P comprises utilizing an extended Katsevich algorithm written:

$$f(x) = \frac{1}{2\pi^2} \int_0^{2\pi} w_{WW}(y(q), x) \int_0^{2\pi} \frac{\partial}{\partial q} D_f(y(q), \Theta(s, x, \gamma))\big|_{q=s} \frac{d\gamma}{\sin\gamma} ds$$

or $$f(x) = -\frac{1}{2\pi^2} \left\{ \left[ \frac{1}{|x - y(s)|} \int_0^{2\pi} D_f(y(s), \Theta(s, x, \gamma)) \frac{d\gamma}{\sin\gamma} \right]\bigg|_{s=s_b(x)}^{s=s_t(x)}, \right.$$

$$- \int_0^{2\pi} \left( \frac{\partial}{\partial s} \frac{1}{|x - y(s)|} \right) w_{WW}(y(s), x) \int_0^{2\pi} D_f(y(s), \Theta(s, x, \gamma)) \frac{d\gamma}{\sin\gamma} ds$$

$$- \int_0^{2\pi} \frac{\beta'_s(s, x) \cdot u(s, x)}{|x - y(s)|} w_{WW}(y(s), x) \int_0^{2\pi} (\nabla_{u(s,x)} D_f)(y(s), \Theta(s, x, \gamma)) \cot\gamma\, d\gamma ds$$

$$- \int_0^{2\pi} \frac{e'_s(s, x) \cdot u(s, x)}{|x - y(s)|} w_{WW}(y(s), x) \int_0^{2\pi} (\nabla_{u(s,x)} D_f)(y(s), \Theta(s, x, \gamma)) d\gamma ds$$

$$- \int_0^{2\pi} \frac{\beta'_s(s, x) \cdot e(s, x)}{|x - y(s)|} w_{WW}(y(s), x) \int_0^{2\pi} \left( \frac{\partial}{\partial \gamma} D_f(y(s), \Theta(s, x, \gamma)) \right) \frac{d\gamma}{\sin\gamma} ds$$

where:

y(s) represents the source focal spot;

x represents the pixel to be reconstructed;

γ represents the fan angle;

β represents the view angle;

α represents the cone angle;

e(s,x)=β(s,x)×u(s,x);

Θ(s,x,y)=cos γβ(s,x)+sin γe(s,x);

$$(\nabla_u D_f)(y(s), \Theta) = \frac{\partial}{\partial t} D_f\big(y(s), \sqrt{1-t^2}\,\Theta + tu\big)\big|_{t=0}, \Theta \in u^{\perp};$$

and $w_{ww}(y(s),x)$ is a view weighting and windowing function.

5. A method in accordance with claim 4 wherein said utilizing an extended Katsevich algorithm comprises utilizing a view weighting and windowing function written:

$$w_{WW}(y(s), x) = \begin{cases} 0 & \text{Condition I} \\ 1 & \text{Condition II} \\ \frac{1}{2} & \text{Condition III} \end{cases}$$

where:

y(s) represents the source focal spot;

x represents the pixel to be reconstructed; and

Condition I corresponds to the situation that both the direct ray and its conjugate ray are outside the Katsevich window;

Condition II corresponds to the situation that either the direct ray or its conjugate ray is within the Katsevich window; and Condition III corresponds to the situation that both the direct and conjugate rays are inside the Katsevich window.

6. A method in accordance with claim 4 wherein said utilizing an extended Katsevich algorithm comprises utilizing a view weighting and windowing function written:

$$w_{WW}(y(s), x) = \begin{cases} 0 & \text{Condition I} \\ 1 & \text{Condition II} \\ \dfrac{\tan^k \alpha_c}{\tan^k \alpha + \tan^k \alpha_c} & \text{Condition III} \end{cases}$$

where:
- y(s) represents the source focal spot;
- x represents the pixel to be reconstructed;
- α represents the cone angle;
- k is a real number larger than 0, and can be adjusted for practical optimization;
- Condition I corresponds to the situation that both the direct ray and its conjugate ray are outside the Katsevich window;
- Condition II corresponds to the situation that either the direct ray or its conjugate ray is within the Katsevich window; and
- Condition III corresponds to the situation that both the direct and conjugate rays are inside the Katsevich window.

7. A method in accordance with claim 4 wherein said utilizing an extended Katsevich algorithm comprises utilizing a view weighting and windowing function written:

$$w_{WW}(y(s), x) = \begin{cases} 0 & \text{Condition I} \\ 1 & \text{Condition II} \\ \dfrac{g_k(\alpha_c)}{g_k(\alpha) + g_k(\alpha_c)} & \text{Condition III} \end{cases}$$

where:
- y(s) represents the source focal spot;
- x represents the pixel to be reconstructed;
- α represents the cone angle;
- k is a real number larger than 0, and can be adjusted for practical optimization;
- $g_k(\alpha)$ is a positive valued monotonically increasing function of α;
- $g_k(\alpha_c)$ is a positive valued monotonically increasing function of $\alpha_c$;
- Condition I corresponds to the situation that both the direct ray and its conjugate ray are outside the Katsevich window;
- Condition II corresponds to the situation that either the direct ray or its conjugate ray is within the Katsevich window; and
- Condition III corresponds to the situation that both the direct and conjugate rays are inside the Katsevich window.

8. A cone-beam volumetric computed tomographic imaging apparatus comprising:

a radiation source;

a detector array; and a processor, said apparatus configured to helically scan an object with the radiation source, said detector array configured to select radiation beams emitted by the radiation source passing through a pixel P, a Tam-window, and a Katsevich window, and said processor configured to filter the selected projection data using a 2π interval for each pixel that is to be reconstructed, and reconstruct an image of the object utilizing a mathematically exact algorithm which includes utilizing the filtered selected projection data including projection data within said Katsevich window and outside the Tam-window.

9. An apparatus in accordance with claim 8 wherein said processor is configured to reconstruct said image of the object utilizing redundant projection data from said selected radiation beams between the Tam-window and the Katsevich window.

10. An apparatus in accordance with claim 8 wherein said detector array is configured to select the radiation beams emitted by the radiation source including direct rays and at least one conjugate ray.

11. An apparatus in accordance with claim 8 wherein the radiation source is an x-ray radiation source.

12. An apparatus in accordance with claim 8 wherein to select radiation beams passing through a pixel P said processor is configured to utilize an extended Katsevich algorithm written:

$$f(x) = -\frac{1}{2\pi^2} \int_0^{2\pi} w_{WW}(y(q), x) \int_0^{2\pi} \frac{\partial}{\partial q} D_f(y(q), \Theta(s, x, \gamma))\Big|_{q=s} \frac{d\gamma}{\sin\gamma} ds \text{ or}$$

$$f(x) = -\frac{1}{2\pi^2} \Bigg\{ \left[\frac{1}{|x-y(s)|} \int_0^{2\pi} D_f(y(s), \Theta(s, x, \gamma)) \frac{d\gamma}{\sin\gamma}\right]\Big|_{s=s_b(x)}^{s=s_1(x)}$$

$$- \int_0^{2\pi} \left(\frac{\partial}{\partial s} \frac{1}{|x-y(s)|}\right) w_{WW}(y(s), x) \int_0^{2\pi} D_f(y(s), \Theta(s, x, \gamma)) \frac{d\gamma}{\sin\gamma} ds$$

$$- \int_0^{2\pi} \frac{\beta'_s(s, x) \cdot u(s, x)}{|x-y(s)|} w_{WW}(y(s), x)$$

$$\int_0^{2\pi} (\nabla_{u(s,x)} D_f)(y(s), \Theta(s, x, \gamma)) \cot\gamma d\gamma ds$$

$$- \int_0^{2\pi} \frac{e'_s(s, x) \cdot u(s, x)}{|x-y(s)|} w_{WW}(y(s), x) \int_0^{2\pi} (\nabla_{u(s,x)} D_f)(y(s), \Theta(s, x, \gamma)) d\gamma ds$$

$$- \int_0^{2\pi} \frac{\beta'_s(s, x) \cdot e(s, x)}{|x-y(s)|} w_{WW}(y(s), x) \int_0^{2\pi} \left(\frac{\partial}{\partial \gamma} D_f(y(s), \Theta(s, x, \gamma))\right) \frac{d\gamma}{\sin\gamma} ds \Bigg\}$$

where:
- y(s) represents the source focal spot;
- x represents the pixel to be reconstructed;
- γ represents the fan angle;
- β represents the view angle;
- α represents the cone angle;
- e(s,x)=β(s,x)×u(s,x);
- Θ(s,x,y)=cos γβ(s,x)+sin γe(s,x);

$$(\nabla_u D_f)(y(s), \Theta) = \frac{\partial}{\partial t} D_f\big(y(s), \sqrt{1-t^2}\,\Theta + tu\big)\Big|_{t=0}, \Theta \in u^\perp;$$

and $w_{ww}(y(s),x)$ is a view weighting and windowing function.

13. An apparatus in accordance with claim 12 wherein said to utilizing an extended Kalsevich algorithm, said processor is configured to utilize a view weighting and windowing function written:

$$w_{WW}(y(s), x) = \begin{cases} 0 & \text{Condition I} \\ 1 & \text{Condition II} \\ \frac{1}{2} & \text{Condition III} \end{cases}$$

where:
  y(s) represents the source focal spot;
  x represents the pixel to be reconstructed;
  Condition I corresponds to the situation that both the direct ray and its conjugate ray are outside the Katsevich window;
  Condition II corresponds to the situation that either the direct ray or its conjugate ray is within the Katsevich window; and
  Condition III corresponds to the situation that both the direct and conjugate rays are inside the Katsevich window.

14. An apparatus in accordance with claim 12 wherein said to utilizing an extended Katsevich algorithm, said processor is configured to utilize a view weighting and windowing function written:

$$w_{WW}(y(q), x) = \begin{cases} 0 & \text{Condition I} \\ 1 & \text{Condition II} \\ \dfrac{\tan^k \alpha_c}{\tan^k \alpha + \tan^k \alpha_c} & \text{Condition III} \end{cases}$$

where:
  y(s) represents the source focal spot;
  x represents the pixel to be reconstructed;
  α represents the cone angle;
  k is a real number larger than 0, and can be adjusted for practical optimization;
  Condition I corresponds to the situation that both the direct ray and its conjugate ray are outside the Katsevich window;
  Condition II corresponds to the situation that either the direct ray or its conjugate ray is within the Katsevich window; and
  Condition III corresponds to the situation that both the direct and conjugate rays are inside the Katsevich window.

15. An apparatus in accordance with claim 12 wherein said to utilizing an extended Katsevich algorithm, said processor is configured to utilize a view weighting and windowing function written:

$$w_{WW}(y(s), x) = \begin{cases} 0 & \text{Condition I} \\ 1 & \text{Condition II} \\ \dfrac{g_k(\alpha_c)}{g_k(\alpha) + g_k(\alpha_c)} & \text{Condition III} \end{cases}$$

where:
  y(s) represents the source focal spot;
  x represents the pixel to be reconstructed;
  α represents the cone angle;
  k is a real number larger than 0, and can be adjusted for practical optimization;
  $g_k(\alpha)$ is a positive valued monotonically increasing function of α;
  $g_k(\alpha_c)$ is a positive valued monotonically increasing function of $\alpha_c$;
  Condition I corresponds to the situation that both the direct ray and its conjugate ray are outside the Katsevich window;
  Condition II corresponds to the situation that either the direct ray or its conjugate ray is within the Katsevich window; and
  Condition III corresponds to the situation that both the direct and conjugate rays are inside the Katsevich window.

16. A computer-usable medium having a computer-readable program embodied thereon, said program configured to instruct a computer to:
  interpolate projection data of a scan of an object wherein the object is helically scanned with a radiation source utilizing a cone-beam volumetric computed tomographic imaging apparatus;
  select radiation beams emitted by the radiation source passing through a pixel P, a Tam-window, and a Katsevich window;
  filter said selected projection data using a 2π interval for each pixel that is to be reconstructed; and
  reconstruct an image of the object utilizing a mathematically exact alorithm and said filtered selected projection data including projection data within said Katsevich window and outside the Tam-window.

17. A medium in accordance with claim 16, wherein to select radiation beams emitted by the radiation source passing through a pixel P, said program is further configured to instruct the computer to utilize an extended Katsevich algorithm written:

$$f(x) = -\frac{1}{2\pi^2} \int_0^{2\pi} w_{WW}(y(q), x) \int_0^{2\pi} \frac{\partial}{\partial q} D_f(y(q), \Theta(s, x, \gamma))\Big|_{q=s} \frac{d\gamma}{\sin\gamma} ds \text{ or}$$

$$f(x) = -\frac{1}{2\pi^2} \Bigg\{ \left[ \frac{1}{|x-y(s)|} \int_0^{2\pi} D_f(y(s), \Theta(s, x, \gamma)) \frac{d\gamma}{\sin\gamma} \right]\Big|_{s=s_b(x)}^{s=s_t(x)}$$

$$- \int_0^{2\pi} \left( \frac{\partial}{\partial s} \frac{1}{|x-y(s)|} \right) w_{WW}(y(s), x) \int_0^{2\pi} D_f(y(s), \Theta(s, x, \gamma)) \frac{d\gamma}{\sin\gamma} ds$$

$$- \int_0^{2\pi} \frac{\beta'_s(s, x) \cdot u(s, x)}{|x-y(s)|} w_{WW}(y(s), x)$$

$$\int_0^{2\pi} (\nabla_{u(s,x)} D_f)(y(s), \Theta(s, x, \gamma)) \cot\gamma \, d\gamma \, ds$$

$$- \int_0^{2\pi} \frac{e'_s(s, x) \cdot u(s, x)}{|x-y(s)|} w_{WW}(y(s), x) \int_0^{2\pi} (\nabla_{u(s,x)} D_f)(y(s), \Theta(s, x, \gamma)) d\gamma \, ds$$

$$- \int_0^{2\pi} \frac{\beta'_s(s, x) \cdot e(s, x)}{|x-y(s)|} w_{WW}(y(s), x) \int_0^{2\pi} \left( \frac{\partial}{\partial \gamma} D_f(y(s), \Theta(s, x, \gamma)) \right) \frac{d\gamma}{\sin\gamma} \Bigg\} ds$$

where:
  y(s) represents the source focal spot;
  x represents the pixel to be reconstructed;
  γ represents the fan angle;
  β represents the view angle;
  α represents the cone angle;
  e(s,x)=β(s,x)×u(s,x);
  Θ(s,x,γ)=cos γβ(s,x)+sin γe(s,x);

$$(\nabla_u D_f)(y(s), \Theta) = \frac{\partial}{\partial t} D_f\left(y(s), \sqrt{1-t^2}\,\Theta + tu\right)\Big|_{t=0}, \Theta \in u^\perp;$$

$w_{ww}(y(s),x)$ is a view weighting and windowing function.

18. A medium in accordance with claim 17, wherein to utilize an extended Katsevich algorithm, said program is further configured to instruct the computer to utilize a view weighting and windowing function written:

$$w_{WW}(y(s), x) = \begin{cases} 0 & \text{Condition I} \\ 1 & \text{Condition II} \\ \frac{1}{2} & \text{Condition III} \end{cases}$$

where:
- y(s) represents the source focal spot;
- x represents the pixel to be reconstructed;
- Condition I corresponds to the situation that both the direct ray and its conjugate ray are outside the Katsevich window;
- Condition II corresponds to the situation that either the direct ray or its conjugate ray is within the Katsevich window; and
- Condition III corresponds to the situation that both the direct and conjugate rays are inside the Katsevich window.

19. An apparatus in accordance with claim 17, wherein to utilize an extended Katsevich algorithm, said program is further configured to instruct the computer to utilize a view weighting and windowing function written:

$$w_{WW}(y(q), x) = \begin{cases} 0 & \text{Condition I} \\ 1 & \text{Condition II} \\ \frac{\tan^k \alpha_c}{\tan^k \alpha + \tan^k \alpha_c} & \text{Condition III} \end{cases}$$

where:
- y(s) represents the source focal spot;
- x represents the pixel to be reconstructed;
- α represents the cone angle;
- k is a real number larger than 0, and can be adjusted for practical optimization;
- Condition I corresponds to the situation that both the direct ray and its conjugate ray are outside the Katsevich window;
- Condition II corresponds to the situation that either the direct ray or its conjugate ray is within the Katsevich window; and
- Condition III corresponds to the situation that both the direct and conjugate rays are inside the Katsevich window.

20. An apparatus in accordance with claim 17, wherein to utilize an extended Katsevich algorithm, said program is further configured to instruct the computer to utilize a view weighting and windowing function written:

$$w_{WW}(y(s), x) = \begin{cases} 0 & \text{Condition I} \\ 1 & \text{Condition II} \\ \frac{g_k(\alpha_c)}{g_k(\alpha) + g_k(\alpha_c)} & \text{Condition III} \end{cases}$$

where:
- y(s) represents the source focal spot;
- x represents the pixel to be reconstructed;
- α represents the cone angle;
- k is a real number larger than 0, and can be adjusted for practical optimization;
- $g_k(\alpha)$ is a positive valued monotonically increasing function of α;
- $g_k(\alpha_c)$ is a positive valued monotonically increasing function of $\alpha_c$;
- Condition I corresponds to the situation that both the direct ray and its conjugate ray are outside the Katsevich window;
- Condition II corresponds to the situation that either the direct ray or its conjugate ray is within the Katsevich window; and
- Condition III corresponds to the situation that both the direct and conjugate rays are inside the Katsevich window.

* * * * *